United States Patent
Chen et al.

(10) Patent No.: US 12,343,344 B2
(45) Date of Patent: Jul. 1, 2025

(54) PHARMACEUTICAL COMBINATION COMPRISING TNO155 AND RIBOCICLIB

(71) Applicant: NOVARTIS AG, Basel (CH)

(72) Inventors: Ying-Nan Pan Chen, Wilmington, DE (US); Huaixiang Hao, Lexington, MA (US); Chen Liu, Wayland, MA (US); Morvarid Mohseni, Boston, MA (US)

(73) Assignee: NOVARTIS AG, Basel (CH)

( * ) Notice: Subject to any disclaimer, the term of this patent is extended or adjusted under 35 U.S.C. 154(b) by 871 days.

(21) Appl. No.: 17/430,219

(22) PCT Filed: Feb. 10, 2020

(86) PCT No.: PCT/IB2020/051031
§ 371 (c)(1),
(2) Date: Aug. 11, 2021

(87) PCT Pub. No.: WO2020/165734
PCT Pub. Date: Aug. 20, 2020

(65) Prior Publication Data
US 2022/0160707 A1     May 26, 2022

Related U.S. Application Data

(60) Provisional application No. 62/804,708, filed on Feb. 12, 2019.

(51) Int. Cl.
*A61K 31/497* (2006.01)
*A61K 31/519* (2006.01)
*A61P 35/00* (2006.01)

(52) U.S. Cl.
CPC .......... *A61K 31/497* (2013.01); *A61K 31/519* (2013.01); *A61P 35/00* (2018.01)

(58) Field of Classification Search
CPC .... A61K 31/497; A61K 31/519; A61K 31/00; A61K 2300/00; A61K 45/06; A61P 35/00
See application file for complete search history.

(56) References Cited

U.S. PATENT DOCUMENTS

| | | |
|---|---|---|
| 2022/0152026 A1 | 5/2022 | Brachmann et al. |
| 2022/0160706 A1 | 5/2022 | Chen et al. |

FOREIGN PATENT DOCUMENTS

| | | |
|---|---|---|
| WO | WO 2010/020675 A1 | 2/2010 |
| WO | WO 2015/107495 A1 | 7/2015 |

(Continued)

OTHER PUBLICATIONS

Tripathy, Debu, et al. "Ribociclib (LEE011): Mechanism of Action and Clinical Impact of This Selective Cyclin-Dependent Kinase 4/6 Inhibitor in Various Solid Tumors." Clinical Cancer Research, vol. 23, No. 13, Jul. 2017, pp. 3251-3262. DOI.org (Crossref), https://doi.org/10.1158/1078-0432.CCR-16-3157. (Year: 2017).*

(Continued)

*Primary Examiner* — Valerie Rodriguez-Garcia
*Assistant Examiner* — Kyle Nottingham
(74) *Attorney, Agent, or Firm* — LATHROP GPM LLP; Brian C. Trinque (57) ABSTRACT

The present invention relates to a pharmaceutical combination comprising TNO155 and ribociclib; pharmaceutical compositions comprising the same; and methods of using such combinations and compositions in the treatment or prevention of conditions in a SHP2 inhibitor combined with CDK4/6 inhibition is beneficial in, for example, the treatment of cancers.

6 Claims, 4 Drawing Sheets

*In vitro* combination benefits of TNO155 and ribociclib in EGFR$^{mut}$ NSCLC cells (56) References Cited

FOREIGN PATENT DOCUMENTS

| WO | WO 2018/130928 A1 | 7/2018 | |
|---|---|---|---|
| WO | WO-2019051084 A1 * | 3/2019 | ........... A61K 31/282 |
| WO | WO 2020/131696 A1 | 6/2020 | |
| WO | WO 2020/131704 A1 | 6/2020 | |
| WO | WO 2020165733 A1 | 8/2020 | |

OTHER PUBLICATIONS

Dempke, Wc M., et al. Targeting SHP-1,2 and SHIP Pathways—a Novel Strategy for Cancer Treatment? Oct. 2018. sussex.figshare. com, https://doi.org/10.1159/000490106']. (Year: 2018).*

Schettini et al., "CDK 4/6 Inhibitors as Single Agent in Advanced Solid Tumors", *Frontiers in Oncology* vol. 8, Article 608, doi: 10.3389/fonc.2018.00608 (2018).

Belikov, Farmatsevticheskaya Khimiya (Pharmaceutical Chemistry), Textbook 2007, Moscow, MEDpress-inform, pp. 27-29.

Kharkevich, Pharmacology, Textbook 2010, $10^{th}$ Edition, pp. 72-82.

Kim et al., "The potent and selective cyclin-dependent kinases 4 and 6 inhibitor ribociclib (LEE011) is a versatile combination partner in preclinical cancer models", *Oncotarget* 9(81):35226-35240 (2018).

Klein et al., "CDK4/6 Inhibitors: The Mechanism of Action May Not Be as Simple as Once Thought", *Cancer Cell* 34:9-20 (2018).

Mashkovsky, Pharmaceuticals Physician's Guide, vol. 1 (2002).

Dempke et al., "Targeting SHP-1, 2 and SHIP Pathways: A Novel Strategy for Cancer Treatment?", *Oncology* 95(5):257-269 (2018).

Giopanou et al., "RAS and BRAF in the foreground for non-small cell lung cancer and colorectal cancer: Similarities and main differences for prognosis and therapies", *Critical Reviews in Oncology/Hematology* 146 (2019).

International Search Report and Written Opinion for International Application No. PCT/IB2020/051031, mailed May 29, 2020, 10 pages.

Tripathy et al., "Ribociclib (LEE011): Mechanism of Action and Clinical Impact of This Selective Cyclin-Dependent Kinase 4/6 Inhibitor in Various Solid Tumors", *Clinical Cancer Research* 23(13):3251-3262 (2017).

Hamilton et al., "Targeting CDK4/6 in patients with cancer", *Cancer Treatment Reviews* 45:129-138 (2016).

* cited by examiner

FIGURE 1

*In vitro* combination benefits of TNO155 and ribociclib in EGFR$^{mut}$ NSCLC cells

FIGURE 2

Prevention of ribociclib-induced Cyclin D1 accumulation by TNO155 in EGFR$^{mut}$ NSCLC cells

FIGURE 3

SHP2i (TNO155 and LWS391) and ribociclib have a combination benefit in NSCLC and CRC cell lines

FIGURE 4

TNO155 and ribociclib is more effective than either single agent in multpile indications in PTX study

PHARMACEUTICAL COMBINATION COMPRISING TNO155 AND RIBOCICLIB

This application is an U.S. National Phase filing of International Application Serial No. PCT/IB2020/051031 filed 10 Feb. 2020 and claims priority from U.S. Provisional Application Ser. No. 62/804,708 filed 12 Feb. 2019, respectively, each of which are incorporated herein by reference in their entireties.

FIELD OF THE INVENTION

The present invention relates to a pharmaceutical combination comprising TNO155 and ribociclib; pharmaceutical compositions comprising the same; and methods of using such combinations and compositions in the treatment or prevention of conditions in which SHP2 inhibition combined with CDK4/6 inhibition is beneficial, for example, in the treatment of cancers.

BACKGROUND OF THE INVENTION

TNO155 is an orally bioavailable, allosteric inhibitor of Src homology-2 domain containing protein tyrosine phsophatase-2 (SHP2, encoded by the PTPN11 gene), which transduces signals from activated receptor tyrosine kinases (RTKs) to downstream pathways, including the mitogen-activated protein kinase (MAPK) pathway. SHP2 has also been implicated in immune checkpoint and cytokine receptor signaling. TNO155 has demonstrated efficacy in a wide range of RTK-dependent human cancer cell lines and in vivo tumor xenografts.

Cyclin D proteins are critical in cancer cell division and complex with the CDK4 and CDK6 protein kinases to promote G1 progression by hyperphosphorylating and activating the retinoblastoma protein (pRb). Ribociclib inhibits CDK4/6 specific phosphorylation of pRb, thereby halting cell cycle progression in the G1 phase. Cyclin D1 is an effector of signaling downstream of mutant EGFR and other RTKs, suggesting that the cyclin D1-CDK4/6 axis plays an important role in proliferation downstream of RTKs.

The combination of the present invention, TNO155 and ribociclib, shows improved efficacy compared to either single agent alone in the treatment of: esophageal or head and neck squamous cell carcinoma; colorectal, ovarian, pancreatic or non-small cell lung cancer; and renal cell carcinoma.

SUMMARY OF THE INVENTION

The present invention provides for a pharmaceutical combination comprising:

(a) a SHP2 inhibitor selected from: (3S,4S)-8-(6-amino-5-((2-amino-3-chloropyridin-4-yl)thio)pyrazin-2-yl)-3-methyl-2-oxa-8-azaspiro[4.5]decan-4-amine (TNO155), or a pharmaceutically acceptable salt thereof, having the structure:

and
8-(6-amino-5-((2-(trifluoromethyl)pyridin-3-yl)thio)pyrazin-2-yl)-8-azaspiro[4.5]decan-1-amine, or a pharmaceutically acceptable salt thereof, having the structure:

and
(b) 7-cyclopentyl-N,N-dimethyl-2-((5-(piperazin-1-yl)pyridin-2-yl)amino)-7H-pyrrolo[2,3-d]pyrimidine-6-carboxamide (ribociclib), or a pharmaceutically acceptable salt thereof, having the structure:

Combinations of TNO155, or a pharmaceutically acceptable salt thereof, and ribociclib, or a pharmaceutically acceptable salt thereof, will also be referred to herein as a "combination of the invention".

In another embodiment of the combination of the invention, TNO155 or a pharmaceutically acceptable salt thereof and ribociclib, or a pharmaceutically acceptable salt thereof, are in the same formulation.

In another embodiment of the combination of the invention, TNO155 or a pharmaceutically acceptable salt thereof and ribociclib or a pharmaceutically acceptable salt thereof are in separate formulations.

In another embodiment, the combination of the invention is for simultaneous or sequential (in any order) administration.

In another embodiment is a method for treating or preventing cancer in a subject in need thereof comprising administering to the subject a therapeutically effective amount of the combination of the invention.

In a further embodiment of the method, the cancer is selected from: esophageal or head and neck squamous cell carcinoma; colorectal, ovarian, pancreatic or non-small cell lung cancer; and renal cell carcinoma.

In a further embodiment of the method, the cancer is selected from colorectal, ovarian, pancreatic and non-small cell lung cancer.

In a further embodiment of the method, the cancer is renal cell carcinoma.

In a further embodiment, the combination of the invention provides for a use in the manufacture of a medicament for treating a cancer selected from: esophageal or head and neck squamous cell carcinoma; colorectal, ovarian, pancreatic or non-small cell lung cancer; and renal cell carcinoma.

In another embodiment is a pharmaceutical composition comprising the combination of the invention.

In a further embodiment, the pharmaceutical composition further comprises one or more pharmaceutically acceptable excipients.

DEFINITIONS

The general terms used hereinbefore and hereinafter preferably have within the context of this disclosure the following meanings, unless otherwise indicated, where more general terms wherever used may, independently of each other, be replaced by more specific definitions or remain, thus defining more detailed embodiments of the invention:

The term "subject" or "patient" as used herein is intended to include animals, which are capable of suffering from or afflicted with a cancer or any disorder involving, directly or indirectly, a cancer. Examples of subjects include mammals, e.g., humans, apes, monkeys, dogs, cows, horses, pigs, sheep, goats, cats, mice, rabbits, rats, and transgenic non-human animals. In an embodiment, the subject is a human, e.g., a human suffering from, at risk of suffering from, or potentially capable of suffering from cancers.

The term "treating" or "treatment" as used herein comprises a treatment relieving, reducing or alleviating at least one symptom in a subject or effecting a delay of progression of a disease. For example, treatment can be the diminishment of one or several symptoms of a disorder or complete eradication of a disorder, such as cancer. Within the meaning of the present disclosure, the term "treat" also denotes to arrest, delay the onset (i.e., the period prior to clinical manifestation of a disease) and/or reduce the risk of developing or worsening a disease.

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The term "combination therapy" or "in combination with" refers to the administration of two or more therapeutic agents to treat a condition or disorder described in the present disclosure (e.g., cancer). Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect.

The term "synergistic effect" as used herein refers to action of two therapeutic agents such as, for example, a compound TNO155 as a SHP2 inhibitor and ribociclib as a CDK4/6 inhibitor, producing an effect, for example, slowing the symptomatic progression of a proliferative disease, particularly cancer, or symptoms thereof, which is greater than the simple addition of the effects of each drug administered by themselves. A synergistic effect can be calculated, for example, using suitable methods such as the Sigmoid-Emax equation (Holford, N. H. G. and Schemer, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

The combination of the invention, TNO155 and ribociclib, is also intended to represent unlabeled forms as well as isotopically labeled forms of the compounds. Isotopically labeled compounds have one or more atoms replaced by an atom having a selected atomic mass or mass number. Examples of isotopes that can be incorporated into TNO155 and ribociclib include isotopes of hydrogen, carbon, nitrogen, oxygen, and chlorine, for example, $^2$H, $^3$H, $^{11}$C, $^{13}$C, $^{14}$C, $^{15}$N, $^{35}$S, $^{36}$Cl. The invention includes isotopically labeled TNO155 and ribociclib, for example into which radioactive isotopes, such as $^3$H and $^{14}$C, or non-radioactive isotopes, such as $^2$H and $^{13}$C, are present. Isotopically labelled TNO155 and ribociclib are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. Isotopically-labeled compounds of the invention can generally be prepared by conventional techniques known to those skilled in the art or by processes analogous to those described in the accompanying Examples using appropriate isotopically-labeled reagents.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of either TNO155 or ribociclib. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in TNO155 or ribociclib is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

DESCRIPTION OF PREFERRED EMBODIMENTS

TNO155 is an investigational agent that is an orally bioavailable small molecule inhibitor of SHP2 activity. SHP2 transduces signaling downstream of activated RTKs. In preclinical models, tumor dependence on RTKs predicts dependence on SH""""""P2.

In one embodiment is a method of treating cancer comprising administering to a subject in need thereof a pharmaceutical composition comprising (3S,4S)-8-(6-amino-5-((2-amino-3-chloropyridin-4-yl)thio)pyrazin-2-yl)-3-methyl-2-oxa-8-azaspiro[4.5]decan-4-amine, or pharmaceutically acceptable salt thereof, in combination with a second therapeutic agent.

In a further embodiment, the cancer is selected from: esophageal or head and neck squamous cell carcinoma; colorectal, ovarian, pancreatic or non-small cell lung cancer; and renal cell carcinoma.

In a further embodiment, the cancer is esophageal cancer.

In a further embodiment, the cancer is head and neck squamous cell carcinoma.

In a further embodiment, the cancer is colorectal cancer.

In a further embodiment, the cancer is ovarian cancer.

In a further embodiment, the cancer is pancreatic cancer.

In a further embodiment, the cancer is non-small cell lung cancer.

In a further embodiment, the cancer is rnal cell carcinoma.

In a further embodiment, (3S,4S)-8-(6-amino-5-((2-amino-3-chloropyridin-4-yl)thio)pyrazin-2-yl)-3-methyl-2-oxa-8-azaspiro[4.5]decan-4-amine, or pharmaceutically acceptable salt thereof, and the second therapeutic agent are are administered simultaneously, separately or over a period of time.

In a further embodiment, (3S,4S)-8-(6-amino-5-((2-amino-3-chloropyridin-4-yl)thio)pyrazin-2-yl)-3-methyl-2-oxa-8-azaspiro[4.5]decan-4-amine, or pharmaceutically acceptable salt thereof, administered to the subject in need therof is effective to treat the cancer.

In a further embodiment, the method comprises a second therapeutic agent.

In a further embodiment, the amount of (3S,4S)-8-(6-amino-5-((2-amino-3-chloropyridin-4-yl)thio)pyrazin-2-yl)-3-methyl-2-oxa-8-azaspiro[4.5]decan-4-amine, or pharmaceutically acceptable salt thereof, and the second therapeutic agent, administered to the subject in need therof, is effective to treat the cancer.

In a further embodiment, the second therapeutic agent is a CDK4/6 inhibitor.

In a further embodiment, the CDK4/6 inhibitor is 7-cyclopentyl-N,N-dimethyl-2-((5-(piperazin-1-yl)pyridin-2-yl)amino)-7H-pyrrolo[2,3-d]pyrimidine-6-carboxamide, or a pharmaceutically acceptable salt thereof.

In a further embodiment, (3S,4S)-8-(6-amino-5-((2-amino-3-chloropyridin-4-yl)thio)pyrazin-2-yl)-3-methyl-2-oxa-8-azaspiro[4.5]decan-4-amine is administered orally at a dose of about 1.5 mg per day, or 3 mg per day, or 6 mg per day, or 10 mg per day, or 20 mg per day, or 30 mg per day, or 40 mg per day, or 50 mg per day, or 60 mg per day, or 70 mg per day, or 80 mg per day, or 90 mg per day, or 100 mg per day In a further embodiment, (3S,4S)-8-(6-amino-5-((2-amino-3-chloropyridin-4-yl)thio)pyrazin-2-yl)-3-methyl-2-oxa-8-azaspiro[4.5]decan-4-amine is administered orally at a dose per day of 20 mg on a 21 day cycle of 2 weeks on drug followed by 1 week off drug.

In a further embodiment, 7-cyclopentyl-N,N-dimethyl-2-((5-(piperazin-1-yl)pyridin-2-yl)amino)-7H-pyrrolo[2,3-d] pyrimidine-6-carboxamide is administered orally at a dose of about 100 mg per day, or 200 mg per day, or 300 mg per day, or 400 mg per day, or 500 mg per day, or 600 mg per day.

In a further embodiment, 7-cyclopentyl-N,N-dimethyl-2-((5-(piperazin-1-yl)pyridin-2-yl)amino)-7H-pyrrolo[2,3-d] pyrimidine-6-carboxamide is administered orally at 200 mg for 21 days.

In a further embodiment, 7-cyclopentyl-N,N-dimethyl-2-((5-(piperazin-1-yl)pyridin-2-yl)amino)-7H-pyrrolo[2,3-d] pyrimidine-6-carboxamide is administered orally at 300 mg for 21 days followed by 7 days off treatment.

In a further embodiment, 7-cyclopentyl-N,N-dimethyl-2-((5-(piperazin-1-yl)pyridin-2-yl)amino)-7H-pyrrolo[2,3-d] pyrimidine-6-carboxamide is administered orally at 600 mg for 21 days followed by 7 days off treatment.

In another embodiment is a method of treating cancer comprising administering, to a patient in need thereof, (3S,4S)-8-(6-amino-5-((2-amino-3-chloropyridin-4-yl)thio) pyrazin-2-yl)-3-methyl-2-oxa-8-azaspiro[4.5]decan-4-amine is administered orally at a dose of about 1.5 mg per day, or 3 mg per day, or 6 mg per day, or 10 mg per day, or 20 mg per day, or 30 mg per day, or 40 mg per day, or 50 mg per day, or 60 mg per day, or 70 mg per day, or 80 mg per day, or 90 mg per day, or 100 mg per day.

In a further embodiment, (3S,4S)-8-(6-amino-5-((2-amino-3-chloropyridin-4-yl)thio)pyrazin-2-yl)-3-methyl-2-oxa-8-azaspiro[4.5]decan-4-amine is administered orally at a dose per day of 20 mg on a 21 day cycle of 2 weeks on drug followed by 1 week off drug.

In a further embodiment, the cancer is selected from: esophageal or head and neck squamous cell carcinoma; colorectal, ovarian, pancreatic or non-small cell lung cancer; and renal cell carcinoma.

In a further embodiment, the cancer is esophageal cancer.

In a further embodiment, the cancer is head and neck squamous cell carcinoma.

In a further embodiment, the cancer is colorectal cancer.

In a further embodiment, the cancer is ovarian cancer.

In a further embodiment, the cancer is pancreatic cancer.

In a further embodiment, the cancer is non-small cell lung cancer.

In a further embodiment, the cancer is rnal cell carcinoma.

In a further embodiment, the method comprises a second therapeutic agent.

In a further embodiment, (3S,4S)-8-(6-amino-5-((2-amino-3-chloropyridin-4-yl)thio)pyrazin-2-yl)-3-methyl-2-oxa-8-azaspiro[4.5]decan-4-amine, or pharmaceutically acceptable salt thereof, and the second therapeutic agent are are administered simultaneously, separately or over a period of time.

In a further embodiment, the second therapeutic agent is a CDK4/6 inhibitor.

In a further embodiment, the CDK4/6 inhibitor is 7-cyclopentyl-N,N-dimethyl-2-((5-(piperazin-1-yl)pyridin-2-yl)amino)-7H-pyrrolo[2,3-d]pyrimidine-6-carboxamide, or a pharmaceutically acceptable salt thereof.

Ina further embodiment, 7-cyclopentyl-N,N-dimethyl-2-((5-(piperazin-1-yl)pyridin-2-yl)amino)-7H-pyrrolo[2,3-d]pyrimidine-6-carboxamide is administered orally at a dose of about 100 mg per day, or 200 mg per day, or 300 mg per day, or 400 mg per day, or 500 mg per day, or 600 mg per day.

In a further embodiment, 7-cyclopentyl-N,N-dimethyl-2-((5-(piperazin-1-yl)pyridin-2-yl)amino)-7H-pyrrolo[2,3-d]pyrimidine-6-carboxamide is administered orally at 600 mg for 21 days followed by 7 days off treatment.

In one embodiment, with respect to the pharmaceutical combination of the invention, is a pharmaceutical combination comprising (3S,4S)-8-(6-amino-5-((2-amino-3-chloropyridin-4-yl)thio)pyrazin-2-yl)-3-methyl-2-oxa-8-azaspiro[4.5]decan-4-amine, or pharmaceutically acceptable salt thereof, and 7-cyclopentyl-N,N-dimethyl-2-((5-(piperazin-1-yl)pyridin-2-yl)amino)-7H-pyrrolo[2,3-d]pyrimidine-6-carboxamide, or a pharmaceutically acceptable salt thereof.

In a further embodiment, (3S,4S)-8-(6-amino-5-((2-amino-3-chloropyridin-4-yl)thio)pyrazin-2-yl)-3-methyl-2-oxa-8-azaspiro[4.5]decan-4-amine, or a pharmaceutically acceptable salt thereof, and 7-cyclopentyl-N,N-dimethyl-2-((5-(piperazin-1-yl)pyridin-2-yl)amino)-7H-pyrrolo[2,3-d]pyrimidine-6-carboxamide, or a pharmaceutically acceptable salt thereof, are administered separately, simultaneously or sequentially, in any order.

In a further embodiment, the pharmaceutical combination is for oral administration.

In a further embodiment, (3S,4S)-8-(6-amino-5-((2-amino-3-chloropyridin-4-yl)thio)pyrazin-2-yl)-3-methyl-2-oxa-8-azaspiro[4.5]decan-4-amine is in an oral dose form.

In a further embodiment, 7-cyclopentyl-N,N-dimethyl-2-((5-(piperazin-1-yl)pyridin-2-yl)amino)-7H-pyrrolo[2,3-d]pyrimidine-6-carboxamide is in an oral dose form.

In another embodiment, is a pharmaceutical composition comprising a pharmaceutical combination of (3S,4S)-8-(6-amino-5-((2-amino-3-chloropyridin-4-yl)thio)pyrazin-2-yl)-3-methyl-2-oxa-8-azaspiro[4.5]decan-4-amine, or pharmaceutically acceptable salt thereof, and 7-cyclopentyl-N,N-dimethyl-2-((5-(piperazin-1-yl)pyridin-2-yl)amino)-7H-pyrrolo[2,3-d]pyrimidine-6-carboxamide, or a pharmaceutically acceptable salt thereof and at least one pharmaceutically acceptable carrier.

In a further embodiment, is a pharmaceutical combination of (3S,4S)-8-(6-amino-5-((2-amino-3-chloropyridin-4-yl)thio)pyrazin-2-yl)-3-methyl-2-oxa-8-azaspiro[4.5]decan-4-amine, or pharmaceutically acceptable salt thereof, and 7-cyclopentyl-N,N-dimethyl-2-((5-(piperazin-1-yl)pyridin-2-yl)amino)-7H-pyrrolo[2,3-d]pyrimidine-6-carboxamide, or a pharmaceutically acceptable salt thereof, for use in the treatment of esophageal or head and neck squamous cell carcinoma.

In another embodiment, is a pharmaceutical combination of (3S,4S)-8-(6-amino-5-((2-amino-3-chloropyridin-4-yl)thio)pyrazin-2-yl)-3-methyl-2-oxa-8-azaspiro[4.5]decan-4-amine, or pharmaceutically acceptable salt thereof, and 7-cyclopentyl-N,N-dimethyl-2-((5-(piperazin-1-yl)pyridin-2-yl)amino)-7H-pyrrolo[2,3-d]pyrimidine-6-carboxamide, or a pharmaceutically acceptable salt thereof, for use in the treatment of colorectal, ovarian, pancreatic or non-small cell lung cancer.

In another embodiment, is a pharmaceutical combination of (3S,4S)-8-(6-amino-5-((2-amino-3-chloropyridin-4-yl)thio)pyrazin-2-yl)-3-methyl-2-oxa-8-azaspiro[4.5]decan-4-amine, or pharmaceutically acceptable salt thereof, and 7-cyclopentyl-N,N-dimethyl-2-((5-(piperazin-1-yl)pyridin-2-yl)amino)-7H-pyrrolo[2,3-d]pyrimidine-6-carboxamide, or a pharmaceutically acceptable salt thereof, for use in the treatment of renal cell carcinoma.

In another embodiment, is a use of the pharmaceutical combination of ((3S,4S)-8-(6-amino-5-((2-amino-3-chloropyridin-4-yl)thio)pyrazin-2-yl)-3-methyl-2-oxa-8-azaspiro[4.5]decan-4-amine, or pharmaceutically acceptable salt thereof, and 7-cyclopentyl-N,N-dimethyl-2-((5-(piperazin-1-yl)pyridin-2-yl)amino)-7H-pyrrolo[2,3-d]pyrimidine-6-carboxamide, or a pharmaceutically acceptable salt thereof, for the manufacture of a medicament for the treatment of a cancer selected from: esophageal or head and neck squamous cell carcinoma; colorectal, ovarian, pancreatic or non-small cell lung cancer; and renal cell carcinoma.

In another embodiment, is a method of treating a cancer selected from: esophageal or head and neck squamous cell carcinoma; colorectal, ovarian, pancreatic or non-small cell lung cancer; and renal cell carcinoma; comprising administrating to a patient in need thereof a pharmaceutical combination of (3S,4S)-8-(6-amino-5-((2-amino-3-chloropyridin-4-yl)thio)pyrazin-2-yl)-3-methyl-2-oxa-8-azaspiro[4.5]decan-4-amine, or pharmaceutically acceptable salt thereof, and 7-cyclopentyl-N,N-dimethyl-2-((5-(piperazin-1-yl)pyridin-2-yl)amino)-7H-pyrrolo[2,3-d]pyrimidine-6-carboxamide, or a pharmaceutically acceptable salt thereof, or a pharmaceutical composition comprising a pharmaceutical combination of (3S,4S)-8-(6-amino-5-((2-amino-3-chloropyridin-4-yl)thio)pyrazin-2-yl)-3-methyl-2-oxa-8-azaspiro[4.5]decan-4-amine, or pharmaceutically acceptable salt thereof, and 7-cyclopentyl-N,N-dimethyl-2-((5-(piperazin-1-yl)pyridin-2-yl)amino)-7H-pyrrolo[2,3-d]pyrimidine-6-carboxamide, or a pharmaceutically acceptable salt thereof and at least one pharmaceutically acceptable carrier.

In another embodiment, is a method of treating a cancer selected from: esophageal or head and neck squamous cell carcinoma; colorectal, ovarian, pancreatic or non-small cell lung cancer; and renal cell carcinoma; comprising administrating to a patient in need thereof a pharmaceutical combination of (3S,4S)-8-(6-amino-5-((2-amino-3-chloropyridin-4-yl)thio)pyrazin-2-yl)-3-methyl-2-oxa-8-azaspiro[4.5]decan-4-amine, or pharmaceutically acceptable salt thereof, and 7-cyclopentyl-N,N-dimethyl-2-((5-(piperazin-1-yl)pyridin-2-yl)amino)-7H-pyrrolo[2,3-d]pyrimidine-6-carboxamide, or a pharmaceutically acceptable salt thereof, or a pharmaceutical composition comprising a pharmaceutical combination of (3 S,4S)-8-(6-amino-5-((2-amino-3-chloropyridin-4-yl)thio)pyrazin-2-yl)-3-methyl-2-oxa-8-azaspiro[4.5]decan-4-amine, or pharmaceutically acceptable salt thereof, and 7-cyclopentyl-N,N-dimethyl-2-((5-(piperazin- 1-yl)pyridin-2-yl)amino)-7H-pyrrolo[2,3-d]pyrimidine-6-carboxamide, or a pharmaceutically acceptable salt thereof and at least one pharmaceutically acceptable carrier.

In another embodiment, (3S,4S)-8-(6-amino-5-((2-amino-3-chloropyridin-4-yl)thio)pyrazin-2-yl)-3-methyl-2-oxa-8-azaspiro[4.5]decan-4-amine is administered orally at a dose of about 1.5 mg per day, or 3 mg per day, or 6 mg per day, or 10 mg per day, or 20 mg per day, or 30 mg per day, or 40 mg per day, or 50 mg per day, or 60 mg per day.

In a further embodiment, 7-cyclopentyl-N,N-dimethyl-2-((5-(piperazin-1-yl)pyridin-2-yl)amino)-7H-pyrrolo[2,3-d]pyrimidine-6-carboxamide is administered orally at a dose of about 100 mg per day, or 200 mg per day, or 300 mg per day, or 400 mg per day, or 500 mg per day, or 600 mg per day.

In a further embodiment, 7-cyclopentyl-N,N-dimethyl-2-((5-(piperazin-1-yl)pyridin-2-yl)amino)-7H-pyrrolo[2,3-d]pyrimidine-6-carboxamide is administered orally at a dose of about 100 mg per day, or 200 mg per day, or 300 mg per day, or 400 mg per day, or 500 mg per day, or 600 mg per day, continuously.

In a further embodiment, 7-cyclopentyl-N,N-dimethyl-2-((5-(piperazin-1-yl)pyridin-2-yl)amino)-7H-pyrrolo[2,3-d]pyrimidine-6-carboxamide is administered orally at a dose of about 100 mg per day, or 200 mg per day, or 300 mg per day, or 400 mg per day, or 500 mg per day, or 600 mg for 21 days followed by 7 days off treatment.

In a further embodiment, 7-cyclopentyl-N,N-dimethyl-2-((5-(piperazin-1-yl)pyridin-2-yl)amino)-7H-pyrrolo[2,3-d]pyrimidine-6-carboxamide is administered orally at 600 mg for 21 days followed by 7 days off treatment.

Pharmacology and Utility

Non-small cell lung cancer—In 2012, approximately 1.8 million people worldwide were diagnosed with lung cancer, and an estimated 1.6 million people died from the disease. Non-small cell lung cancer comprises approximately 85% of lung cancers, with adenocarcinomas and squamous cell carcinomas being the most common subtypes. Standard of care treatment for advanced stage non-small cell lung carcinomas (NSCLCs) that do not harbor genetic alterations in druggable driver oncogenes such as EGFR, ALK, or ROS includes chemotherapy and immunotherapy, administered concurrently or sequentially. While these treatments provide clinical benefit, the majority of patients experience disease progression within a year, and the prognosis for patients with advanced NSCLC remains poor. Immunotherapy for NSCLC with immune checkpoint inhibitors has demonstrated promise, with some NSCLC patients experiencing durable disease control for years. However, such long-term non-progressors are uncommon, and combination treatment strategies that can increase the proportion of patients responding to and achieving lasting remission with immunotherapy using checkpoint inhibitors are urgently needed. Activating mutations in the KRAS oncogene occur in approximately 30% of lung adenocarcinomas, and have been associated with poor outcome in some studies. No approved drugs target mutant KRAS directly, so standard of care for advanced stage KRAS-mutant NSCLC is also chemotherapy and immunotherapy as described above.

Head and neck squamous cell cancer—Squamous cell cancers are the most common cancers occurring in the head and neck, with an estimated worldwide incidence of approximately 686,000 for oropharyngeal and laryngeal cancers combined. Alcohol and tobacco use are the most common risk factors for head and neck squamous cell cancers (HNSCCs), with human papilloma virus (HPV) infection likely also playing a causative role. More than 90% of HNSCCs have overexpression of EGFR or its ligands. For patients with metastatic disease, standard systemic treatment includes platinum-based chemotherapy with or without cetuximab. Historically, median survival with systemic chemotherapy is approximately six months, with only approximately 20% of patients surviving one year. More recently, a survival benefit has been shown for nivolumab, an anti-programmed death-1 (PD-1) antibody, versus standard second-line single agent therapy (docetaxel, methotrexate, or cetuximab) in patients who had progressed on platinum-based chemotherapy. Still, the survival rate at one year for patients treated with nivolumab was only 36%. Therefore, a great need exists for improved treatments for this aggressive and debilitating cancer.

Colorectal cancer—Colorectal cancer (CRC) is the second most common cancer in women and the third most common cancer in men, accounting for an estimated 1.4 million new cancer cases worldwide in 2012. Chromosomal instability and microsatellite instability both play roles in the pathogenesis of CRC. Chromosomal instability is found in approximately 85% of sporadic colorectal cancers and is characterized by mutations in the Wnt pathway genes, APC and CTNNB1. KRAS mutations, occurring most commonly in codon 12 or 13, are present in approximately 45% of these cases and render anti-EGFR therapies ineffective. Microsatellite instability (MSI), arising due to defective DNA mismatch repair, is involved in approximately 15% of sporadic CRCs, as well as CRCs arising in Lynch syndrome due to a germline mutation of a mismatch repair gene. MSI-high CRCs tend to have a better prognosis than non-MSI-high CRC, and also have responded differently to some systemic therapies. Systemic therapy for metastatic CRC includes various agents used alone or in combination, including chemotherapies such as 5-Fluorouracil/leucovorin, capecitabine, oxaliplatin, and irinotecan; anti-angiogenic agents such as bevacizumab and ramucirumab; anti-EGFR agents including cetuximab and panitumumab for KRAS/NRAS wild-type cancers; and immunotherapies including nivolumab and pembrolizumab. Despite multiple active therapies, however, metastatic CRC remains incurable. While CRCs that are deficient in mismatch repair (MSI-high) exhibit high response rates to immune checkpoint inhibitor therapy, mismatch repair proficient CRCs do not. Since KRAS-mutant CRCs are typically mismatch repair proficient and are not candidates for anti-EGFR therapy, this subtype of CRC is particularly in need of improved therapies.

TNO155 is a first-in-class allosteric inhibitor of wild-type SHP2. SHP2 is a ubiquitously expressed non-receptor protein tyrosine phosphatase (PTP) composed of two N-terminal SH2 domains, a classic PTP domain, and a C-terminal tail. The phosphatase activity is auto-inhibited by the two SHP2 domains that bind to the PTP domain (closed conformation). Upon activation of receptor tyrosine kinases (RTKs), SHP2 is recruited to the plasma membrane where it associates with activated RTKs and a number of adaptor proteins to relay signaling by activating the RAS/MAPK pathway. TNO155 binds the inactive, or "closed" conformation of SHP2, thereby preventing its opening into the active conformation. This prevents the transduction of signaling from activated RTKs to the downstream RAS/MAPK pathway.

TNO155 has demonstrated efficacy in a wide range of RTK-dependent human cancer cell lines and in vivo xenografts. Preclinical in vitro and in vivo evaluation of TNO155 demonstrate selective and potent inhibition of the SHP2 phosphatase, in RTK-dependent human cancer models, for example, esophageal, HNSCC and NSCLC. SHP2 inhibition can be measured by assessing biomarkers within the MAPK signaling pathway, such as decreased levels of phosphorylated ERK1/2 (pERK) and downregulation of dual specificity phosphatase 6 (DUSP6) mRNA transcript. In the KYSE-520 (esophageal squamous cell carcinoma) and DETROIT-562 (pharyngeal squamous cell carcinoma) cancer cell lines, the in vitro pERK IC50's were 8 nM (3.4 ng/mL) and 35 nM (14.8 ng/mL) and the antiproliferation IC50's were 100 nM (42.2 ng/mL) and 470 nM (198.3 ng/mL), respectively. The antiproliferative effect of TNO155 was revealed to be most effective in cancer cell lines that are dependent on RTK signaling. In vivo, SHP2 inhibition by orally-administered TNO155 (20 mg/kg) achieved approximately 95% decrease in DUSP6 mRNA transcript in an EGFR-dependent DETROIT-562 cancer cell line and 47% regression when dosed on a twice-daily schedule. Dose fractionation studies, coupled with modulation of the tumor DUSP6 biomarker show that maximal efficacy is achieved when 50% PD inhibition is attained for at least 80% of the dosing interval. Given the extensive cross-talk between the MAPK pathways and the CDK4/6 pathway in cancer cells, the combinations of TNO155 with the selective CDK4/6 inhibitor, Ribociclib, was explored.

Ribociclib (LEE011, Kisqali®) is an orally bioavailable, highly selective small molecule inhibitor of cyclin-dependent kinases 4 and 6 (CDK4/6). Ribociclib has been approved by a number of Health Authorities, including the United States Food and Drug Administration (U.S. FDA) and the European Commission, as an initial endocrine-based therapy for the treatment of postmenopausal women with hormone receptor (HR)-positive, human epidermal growth factor receptor 2 (HER2)-negative advanced or metastatic breast cancer in combination with an aromatase inhibitor (AI) based on a randomized, double-blind, placebo-controlled, international clinical trial (MONALEESA-2 [CLEE011A2301]). On 18 Jul. 2018, the U.S. FDA expanded the indication for ribociclib in combination with an AI to include pre/perimenopausal women with HR-positive, HER2-negative advanced or metastatic breast cancer, as initial endocrine-based therapy. The expanded indication also includes ribociclib in combination with fulvestrant for postmenopausal women with HR-positive, HER2-negative advanced or metastatic breast cancer, as initial endocrine-based therapy or following disease progression on endocrine therapy (MONALEESA-7 [CLEE011E2301] and MONALEESA-3 [CLEE011F2301], respectively). Additional marketing authorizations in HR-positive, HER2-negative advanced or metastatic breast cancer are under review by health authorities worldwide. Additional phase III clinical trials for the treatment of HR-positive breast cancer patients, as well as several other phase I or II clinical studies are being conducted.

Ribociclib inhibits the CDK4/Cyclin D (CCND1) and CDK6/CCND3 enzyme complexes with $IC_{50}$ values of 0.01 and 0.039 µM in biochemical assays, respectively, while showing a high degree of selectivity for CDK4/6 versus other cyclin-dependent kinases. In more than 40 pRb-positive cell lines derived from diverse cancer types, ribociclib inhibited Retinoblastoma protein (pRb) phosphorylation and interfered with G1 to S phase cell cycle progression. In contrast, in lineage-matched pRb-negative cell lines no effect of ribociclib on cell cycle progression was observed.

Ribociclib was well-tolerated in mice and rats for up to 28 days at doses up to 250 mg/kg once daily orally or 150 mg/kg once daily orally respectively, with body weight loss not exceeding 12.5%. However, myelosuppression was observed and correlated with pRb inhibition. Ribociclib has demonstrated in vivo anti-tumor activity in subsets of tumor xenograft models including but not limited to breast, melanoma, neuroblastoma, malignant rhabdoid, lung, pancreas and hematological malignancies. In addition, ribociclib has shown anti-tumor activity when combined with targeted agents which inhibit signaling pathways known to regulate Cyclin D levels, including inhibitors of the RAF, mitogen-activated protein kinase kinase (MEK), phosphoinositide 3-kinase (PI3K) and mammalian target of rapamycin (mTOR) pathways.

The epidermal growth factor receptor (EGFR) is an established critical therapeutic target in NSCLCs harboring activating EGFR mutations. Numerous trials with first (e.g. erlotinib, gefitinib) and second (e.g. afatinib, dacomitinib) generation EGFR inhibitors have been conducted in the EGFR-mutant advanced/unresectable NSCLC population, and have consistently demonstrated superior efficacy of EGFR tyrosine kinase inhibitors (TKIs) over chemotherapy in this population. Resistance to $1^{st}$ generation EGFR TKIs has been shown to arise through the development of an EGFR "gatekeeper" T790M mutation that impairs binding of the TKI, as well as by activation of alternative RTK pathways, including MET and ERBB2 amplification. Clinical trials using $3^{rd}$ generation, irreversible EGFR inhibitors (e.g., osimertinib, rociletinib), which inhibit EGFR activating and gatekeeper mutations have demonstrated efficacy in EGFR T790M-mutant NSCLCs, highlighting their continued dependence on EGFR signaling. Emerging data from cancers that have become resistant to $3^{rd}$ generation inhibitors suggest that these cancers continue to select for activated RTK signaling, with resistance mutations in EGFR (C797S) as well as RTK amplifications (MET, ERBB2, FGFR1) having been described. Limited treatment options are available for patients whose cancers have developed resistance to $1^{st}/2^{nd}$ and $3^{rd}$ generation EGFR TKIs. Since SHP2 transduces EGFR signaling, and preclinical models have demonstrated a strong correlation between RTK dependence and SHP2 dependence, TNO155 is predicted to provide clinical benefit in these cancers whether resistance is driven by signaling from EGFR or another RTK.

More than 90% of head and neck cancers are characterized by overexpression or amplification of EGFR; amplification/overexpression of other RTKs, particularly FGFRs, and their ligands is also common. Inhibition of EGFR with cetuximab in advanced HNSCCs has also demonstrated clinical benefit, though disease control is not durable. The modest efficacy of EGFR inhibition in HNSCC may be related to compensatory signaling through other RTKs, which would be predicted to be abrogated by SHP2 inhibition with TNO155 treatment. In addition, preclinical testing identified head and neck cancer cells as the lineage with the highest frequency of sensitivity to SHP2 inhibition.

Patients with metastatic or unresectable RTK-driven cancers such as anaplastic lymphoma kinase (ALK)-rearranged NSCLC or stem cell factor receptor (KIT)-mutant gastrointestinal stromal tumor (GIST) derive benefit from molecules directly targeting these RTKs, but resistance to these agents invariably occurs. Mechanisms of resistance frequently include drug-resistant mutations in the targeted RTK and/or activation of bypass RTK pathways; in most cases, further treatment options are limited. Targeting SHP2 with TNO155 is a rational approach in such RTK-dependent cancers.

Cyclin D proteins are critical in cancer cell division and complex with the CDK4 and CDK6 protein kinases to promote G1 progression by hyperphosphorylating and activating the retinoblastoma protein (pRb). Cyclin D1 is an effector of signaling downstream of mutant EGFR and other RTKs, suggesting that the cyclin D1-CDK4/6 axis plays an important role in proliferation downstraem of RTKs.

The preclinical data presented in the examples, below, provide in vitro and in vivo evidence that the combination of the SHP2 inhibitor, TNO155 and the CDK4/6 inhibitor, Ribociclib, exert a significant combination benefit across multiple cancer lineages. In vitro, TNO155 and another selective SHP2 inhibitor, LWS391 were evaluated in four NSCLC and one CRC model. The combination of SHP2 inhibitors with ribociclib demonstrated enhanced anti-cell proliferation effects than either single agent did. In vivo, the combination of TNO155 and Ribociclib was evaluated in a broad panel of different lineages of human primary xenografts that were implanted into immunecompromised mice. In all the lineages evaluated for combination efficacy (NSCLC, CRC, HNSCC, Esoph SCC and Renal) the time to tumor progression was significantly extended when the TNO155 and Ribociclib combination were administered. On the basis of the inhibitory studies described in the "Examples" section below, in vivo and in vitro data show improved efficacy of the combination of TNO155 and ribociclib compared to either single agent across several indications.

Pharmaceutical Compositions

In another aspect, the present invention provides pharmaceutically acceptable compositions which comprise a therapeutically-effective amount TNO155 and ribociclib, formulated together with one or more pharmaceutically acceptable carriers (additives) and/or diluents. As described in detail below, the pharmaceutical compositions of the present invention may be specially formulated for administration in solid or liquid form, including those adapted for oral administration, for example, drenches (aqueous or non-aqueous solutions or suspensions), tablets, e.g., those targeted for buccal, sublingual, and systemic absorption, boluses, powders, granules, pastes for application to the tongue.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. The pharmaceutically acceptable salt of TNO155 and ribociclib, for example, is succinate.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution, suspension or solid dispersion in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of the combination of the invention will be that amount of each compound which is the lowest dose effective to produce a therapeutic effect. Such an effective dose will generally depend upon the factors described above.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents.

EXAMPLES

TNO155 and Ribociclib (3S,4S)-8-(6-amino-5-((2-amino-3-chloropyridin-4-yl)thio)pyrazin-2-yl)-3-methyl-2-oxa-8-azaspiro[4.5]decan-4-amine (TNO155) and 8-(6-amino-5-((2-(trifluoromethyl)pyridin-3-yl)thio)pyrazin-2-yl)-8-azaspiro[4.5]decan-1-amine are synthesized according to example 69 and example 1 of WO2015/107495, respectively. 7-cyclopentyl-N,N-dimethyl-2-((5-(piperazin-1-yl)pyridin-2-yl)amino)-7H-pyrrolo[2,3-d]pyrimidine-6-carboxamide (ribociclib) is synthesized according to example 74 of WO2010/020675.

The utility of TNO155 and ribociclib described herein can be evidenced by testing in the following examples.

Example 1

Figure 1:
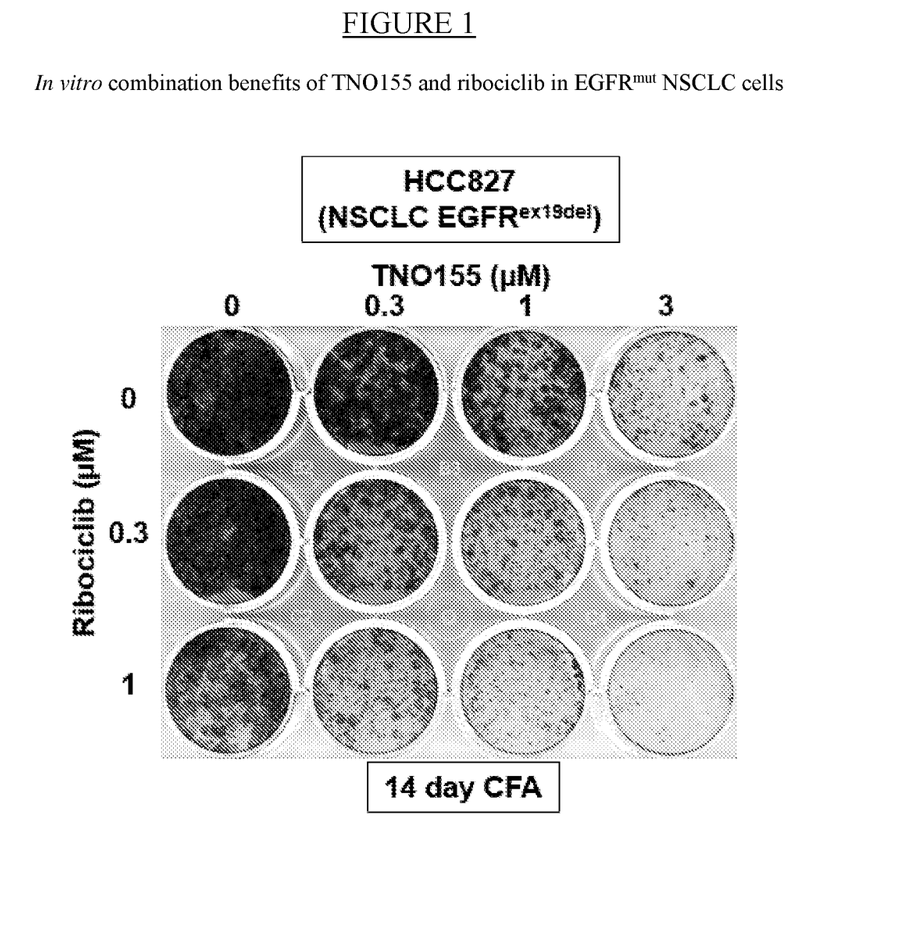
FIG. 1: In vitro combination benefits of TNO155 and robociclib in EGFR$^{mut}$ NSCLC cells.

In Vitro Combination Benefits of TNO155 and Ribociclib in EGFR$^{mut}$ NSCLC Cells Ten thousand HCC827 cells in 2 mL growth media were seeded in each well of 6-well plates. A day later, indicated concentrations of TNO155 or ribociclib or the combination were added. After 14 days, cells were washed with phosphate buffered saline (PBS) and stained with 2 mL of crystal violet staining buffer (1% crystal violet, 1% paraformaldehyde, 1% methanol in PBS). After 10 minute incubation, the crystal violet staining buffer was aspirated, and the cells were washed with PBS twice and water once (5 minutes for each wash). The plates were dried and the images were taken by an EPSON scanner. There is anti-proliferation combination benefit between TNO155 and ribociclib in multiple concentrations.

Example 2

Figure 2:
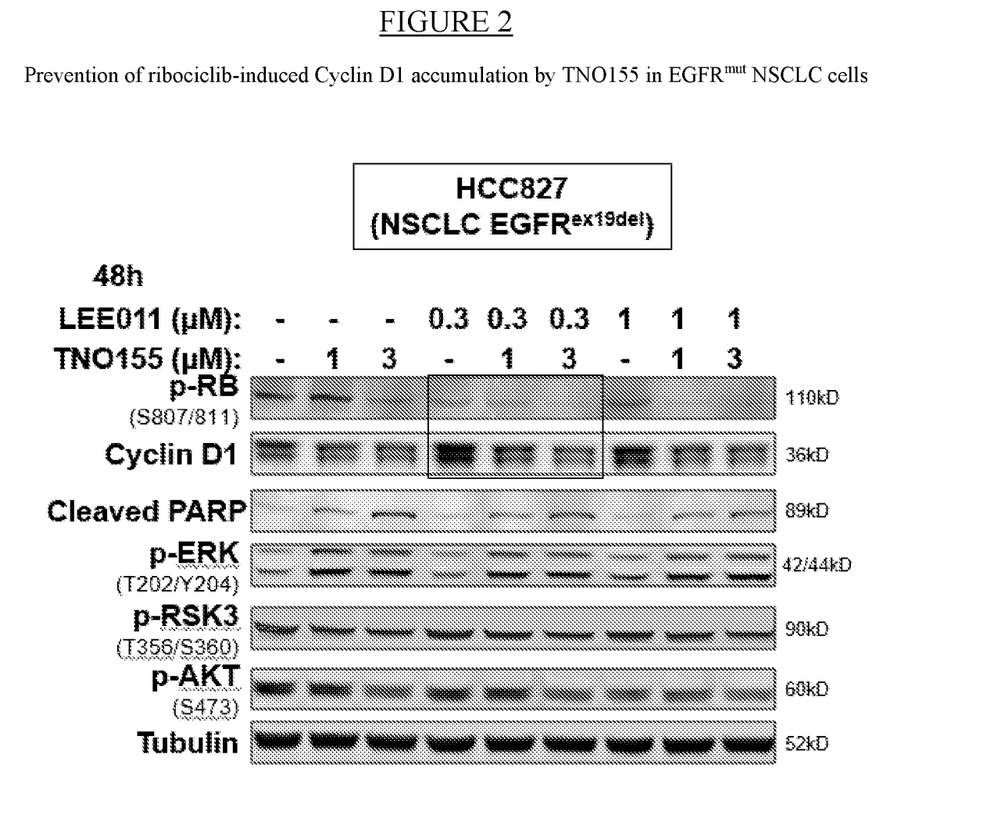
FIG. 2: Prevention of ribociclib-induced Cyclin D1 accumulation by TNO155 in EGFR$^{mut}$ NSCLC cells.

Prevention of Ribociclib-Induced Cyclin D1 Accumulation by TNO155 in EGFR$^{mut}$ NSCLC Cells HCC827 cells were plated in 6-well plates at a density of $2\times10^5$ cells/well in 2 ml of complete culture medium. 24 hours later, cells were treated with indicated concentrations of TNO155 or ribociclib or the combination. 48 hours after the treatment, cells were harvested in freshly prepared RIPA cell lysis buffer supplemented with Protease and Phosphatase Inhibitor Cocktail. Proteins extracted from cell lysates were separated by electrophoresis using a NuPAGE 4-12% Bis-Tis gel and were transferred to nitrocellulose membranes, followed by standard immunobloting procedures. The primary antibodies used were all from Cell Signaling Technology with the following catalog numbers: phospho-RB (S807/811, #8516), Cyclin D1 (#2978), cleaved PARP (#9546), phospho-ERK (T202/Y204, #4370), phospho-RSK3 (T356/S360, #9348), phospho-AKT (S473, #4060) and Tubulin (#3873). The signals were visualized by simantanous incubation with goat anti-rabbit secondary antibodies conjugated with Alexa Fluor® 700 and the goat anti-mouse secondary antibody conjugated with IRDye 800 CW for Tubulin (protein loading control) and scanning with an Odyssey Infrared Imager System.

See results in FIG. 2, showing a prevention of ribociclib-induced cyclin D1 accumulation by TNO155 and a better p-RB inhibition by combining ribociclib and TNO155 compared with either ribociclib or TNO155 alone.

Example 3

Figure 3:
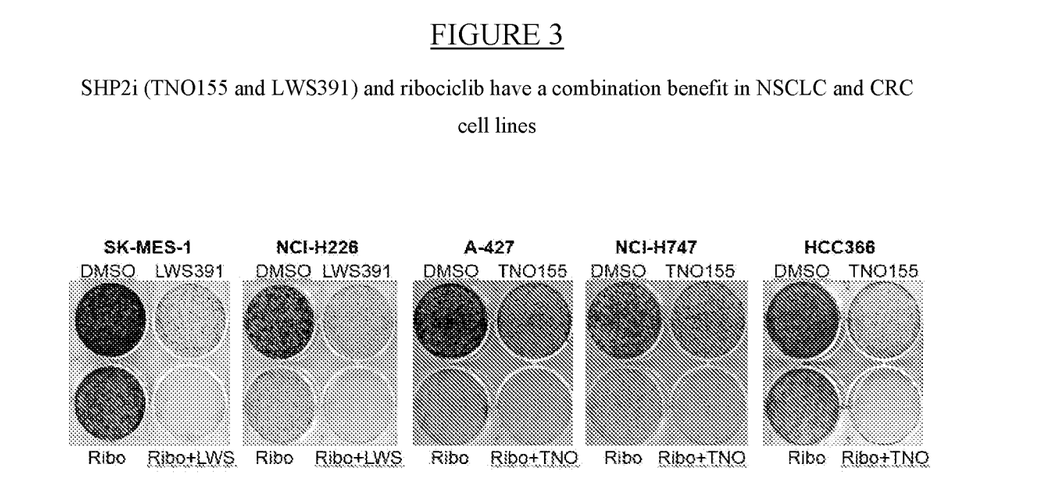
FIG. 3: SHP2i (TNO155 and LWS391) and ribociclib have a combination benefit in NSCLC and CRC cell lines.

SHP2i (TNO155 or LWS391) and Ribociclib have a Combination Benefit in NSCLC and CRC Cell Lines ~10,000 cells in 2 mL growth media were seeded in each well of 6-well plates. A day later, TNO155 or LWS391 or ribociclib, all dissolved in DMSO, were added to the indicated final concentrations. Compounds were replenished every 7 days. After 7-14 days, when cells in the DMSO-treated groups reached a desired confluence, cells were washed with phosphate buffered saline (PBS) and stained with 2 mL of crystal violet staining buffer (1% crystal violet, 1% paraformaldehyde, 1% methanol in PBS). After 10 minute incubation, the crystal violet staining buffer was aspirated, and the cells were washed with PBS twice and water once (5 minutes for each wash). The plates were dried and the images were taken by an EPSON scanner. Cancer cell lines tested were: SK-MES-1 (NSCLC, EGFR WT); NCI-H226 (NSCLC EGFR WT); A-427 (NSCLC, KRAS G12D); NCI-H747 (CRC, KRAS G13D); and HCC366 (NSCLC, EGFR WT, 1 µM TNO155.

See results in FIG. 3, the in vitro combination benefits of an allosteric SHP2 inhibitor, TNO155 or LWS391, and ribociclib were evaluated in a 7~14 day two-dimensional colony formation assay with a panel of NSCLC and CRC cell lines. The combination of TNO155 or LWS391 at 1 or 3 µM and ribociclib at 1 µM impaired colony formation better than either single agent did in three EGFR/ALK/KRAS wild-type NSCLC cell lines, SK-MES-1 and NCI-H226 and HCC366, as well as in two KRAS-mutant cell lines, A-427 (NSCLC) and NCI-H747 (CRC).

Example 4

Figure 4:
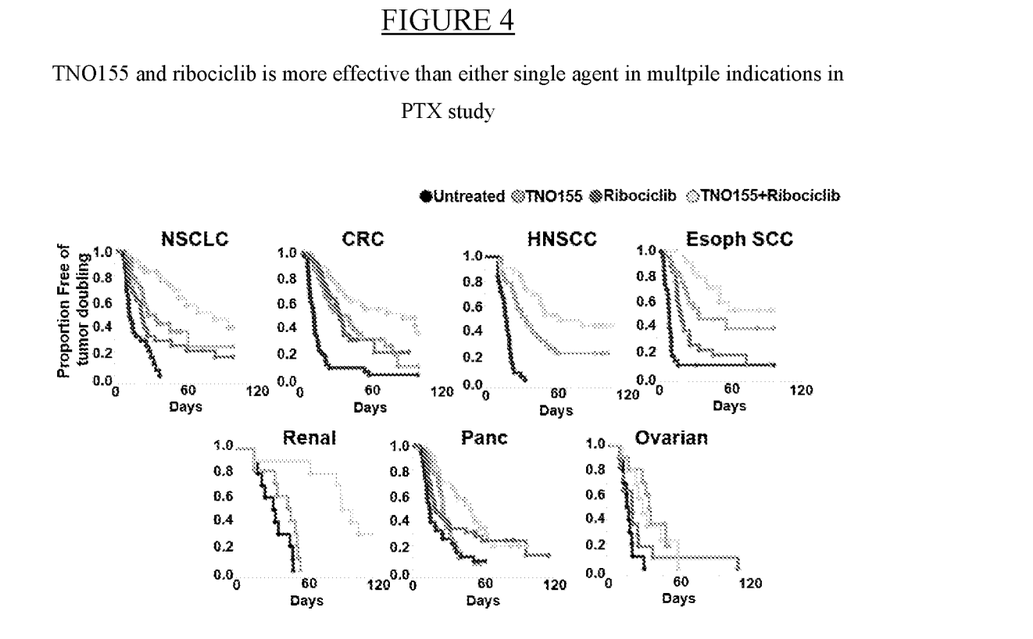
FIG. 4: TNO155 and ribociclib is more effective than either single agent in multiple indications in PTX study.

Combination Benefit of TNO155 and Ribociclib in Primary Human Xenograft Models of Multiple Lineages Implanted into Immunecompromised Nu/Nu Mice Patient-derived xenograft (PDX) models of human non-small cell lung cancer (NSCLC), colorectal cancer (CRC), head and neck cancer (HNSCC), pancreatic cancer (Panc), esophageal cancer (Esoph SCC), renal cancer, and ovarian cancer, were established by direct implantation of patient tumor tissue subcutaneously into nude mice. For each lineage, the number of human primary models evaluated were: NSCLC=32 models, CRC=38 models, HNSCC=33 models, Panc=21 models, Esoph SCC=30 models, renal=21 models, ovarian=18 models. TNO155 and ribociclib were administered daily by oral gavage at well-tolerated dose levels. TNO155 was administered at the tumoristatic dose of 10 mg/kg BID, ribociclib was dosed at 75 mg/kg QD, a dose which achieves similar exposures in mice to those achieved in humans at the clinically relevant dose of 400 mg QD. The combination of TNO155 and ribociclib was conducted at the single agent dose levels and was found to be well-tolerated. Combination benefit of TNO155 with ribocicilib was assessed by evaluating the proportion of tumor models that were free of tumor doubling from the population of primary tumor xenografts undergoing treatment.

See results in FIG. 4, showing Kaplan-Meier graphs depicting the proportion of tumors for each cancer type that have not doubled, plotted over time. The combination of TNO155 and ribociclib is more effective than TNO155 or ribociclib monotherapy in multiple indications, noteably, NSCLC, CRC, HNSCC, Esoph SCC and renal cancer.

Example 5

The initial regimen for TNO155 in combination with ribociclib is based on data from the TNO155 first-in-human study, CTNO155X2101. Initially, TNO155 is dosed daily (QD) 2 weeks on/1 week off on a 21-day cycle (starting at 20 mg QD). Ribociclib is dosed at 200 mg QD continuous on a 21-day cycle which is less than 50% of both the daily and total per cycle dose of the standard labeled dose of 600 mg QD, 3 weeks on/1 week off. Further dosing schedules include: (i) TNO155 QD 2 weeks on/1 week off+ribociclib QD continuous, on a 21-day cycle; (ii) TNO155 QD 3 weeks on/1 week off+ribociclib QD continuous, on a 28-day cycle; (iii) TNO155 QD 3 weeks on/1 week off+ribociclib QD 3 weeks on/1 week off, on a 28-day cycle; (iv) TNO155 QD continuous+ribociclib QD continuous, on a 28-day cycle; (v) TNO155 QD continuous+ribociclib QD, 3 weeks on/1 week off, on a 28-day cycle; and/or (vi) BID schedules of TNO155 and/or ribociclib may also be explored on any of these dosing schedules.

Patients harboring advanced solid tumors (with evaluable disease) fitting into one of the following groups, are treated: i). advanced NSCLC, after progression on or intolerance to platinum-containing combination chemotherapy and anti-PD-1 or anti-PD-L1 therapy; ii). advanced HNSCC or esophageal SCC, after progression on or intolerance to platinum-containing combination therapy and anti-PD-1 or anti-PD-L1 therapy, where such therapy is available and considered standard-of-care (SOC) therapy per local guidelines. Dose expansion treats patients harboring advanced solid tumors, with at least one measurable lesion, who fit into one of the following groups: i). advanced EGFR WT, ALK WT, KRAS WT NSCLC after progression on or intolerance to platinum-containing chemotherapy and anti-PD-1 or anti-PD-L1 therapy, where such therapy is available and considered SOC; ii). advanced CRC harboring a KRAS codon 12, 13, or 61 mutation, after progression on or intolerance to SOC per local guidelines.

It is understood that the Examples and embodiments described herein are for illustrative purposes only and that various modifications or changes in light thereof will be suggested to persons skilled in the art and are to be included within the spirit and purview of this application and scope of the appended claims.

What is claimed is:
1. A method of treating cancer comprising administering to a subject in need thereof comprising (3S,4S)-8-(6-amino-5-((2-amino-3-chloropyridin-4-yl)thio) pyrazin-2-yl)-3-methyl-2-oxa-8-azaspiro [4.5]decan-4-amine, or a pharmaceutically acceptable salt thereof, in combination with a second therapeutic agent,
wherein the second therapeutic agent is the CDK4/6 inhibitor 7-cyclopentyl-N,N-dimethyl-2-((5-(piper- azin-1-yl) pyridin-2-yl)amino)-7H-pyrrolo [2,3-d]pyrimidine-6-carboxamide, or a pharmaceutically acceptable salt thereof;

wherein the cancer is selected from the group consisting of esophageal or head and neck squamous cell carcinoma; colorectal or non-small cell lung cancer; and renal cell carcinoma; and wherein the amount of (3S,4S)-8-(6-amino-5-((2-amino-3-chloropyridin-4-yl)thio) pyrazin-2-y)-3-methyl-2-oxa-8-azaspiro [4.5]decan-4-amine, or a pharmaceutically acceptable salt thereof, and the amount of the second therapeutic agent administered to the subject in need thereof are effective to treat the cancer.

2. The method according to claim 1, wherein (3S,4S)-8-(6-amino-5-((2-amino-3-chloropyridin-4-yl)thio) pyrazin-2-yl)-3-methyl-2-oxa-8-azaspiro [4.5]decan-4-amine, or a pharmaceutically acceptable salt thereof, and the second therapeutic agent are administered simultaneously, separately or over a period of time.

3. The method according to claim 1, wherein (3S,4S)-8-(6-amino-5-((2-amino-3-chloropyridin-4-yl)thio) pyrazin-2-yl)-3-methyl-2-oxa-8-azaspiro [4.5]decan-4-amine, or a pharmaceutically acceptable salt thereof, and the second therapeutic agent are administered sequentially.

4. The method according to claim 1 wherein (3S,4S)-8-(6-amino-5-((2-amino-3-chloropyridin-4-yl)thio) pyrazin-2-yl)-3-methyl-2-oxa-8-azaspiro [4.5]decan-4-amine is administered orally at a dose of about 1.5 mg per day, 3 mg per day, 6 mg per day, 10 mg per day, 20 mg per day, 30 mg per day, 40 mg per day, 50 mg per day, or 60 mg per day.

5. The method of claim 1 wherein 7-cyclopentyl-N,N-dimethyl-2-((5-(piperazin-1-yl) pyridin-2-yl)amino)-7H-pyrrolo [2,3-d]pyrimidine-6-carboxamide is administered orally at a dose of about 100 mg per day, 200 mg per day, 300 mg per day, 400 mg per day, 500 mg per day, or 600 mg per day.

6. The method of claim 5 wherein 7-cyclopentyl-N,N-dimethyl-2-((5-(piperazin-1-yl) pyridin-2-yl)amino)-7H-pyrrolo [2,3-d]pyrimidine-6-carboxamide is administered orally at 600 mg for 21 days followed by 7 days off treatment.

* * * * *